United States Patent [19]

Ohsuka

[11] Patent Number: 5,990,484
[45] Date of Patent: Nov. 23, 1999

[54] METHOD AND APPARATUS FOR MEASURING FLUORESCENCE

[75] Inventor: Shinji Ohsuka, Shizuoka, Japan

[73] Assignee: Laboratory of Molecular Biophotonics, Shizuoka, Japan

[21] Appl. No.: 09/170,998

[22] Filed: Oct. 14, 1998

[30] Foreign Application Priority Data

Oct. 29, 1997 [JP] Japan ..................................... 9-297321

[51] Int. Cl.$^6$ ................................................. G01N 21/64
[52] U.S. Cl. .................................. 250/458.1; 250/459.1; 356/318
[58] Field of Search .................................. 356/317, 318, 356/417; 250/458.1, 459.1, 461.1, 461.2

[56] References Cited

U.S. PATENT DOCUMENTS

| | | | |
|---|---|---|---|
| 4,855,930 | 8/1989 | Chao et al. | 364/497 |
| 5,694,211 | 12/1997 | Ohsuka et al. | 356/218 |

FOREIGN PATENT DOCUMENTS

| | | |
|---|---|---|
| 7167709 | 7/1995 | Japan . |
| 2162943 | 2/1986 | United Kingdom . |
| 9319358 | 9/1993 | WIPO . |

OTHER PUBLICATIONS

Birch et al., "A Single–Photon Counting Fluorescence Decay–Time Spectrometer", Journal of Physics E: Scientific Instruments, vol. 10, Feb. 1977, pp. 1044–1049.

Davis et al., "Correction Methods for Photon Pile–Up in Lifetime Determination by Single–Photon Counting", Oct. 1969, pp. 101–109.

Coates, "The Correction for Photon 'Pile–Up' In the Measurement of Radiative Lifetimes", Journal of Scientific Instruments (Journal of Physics E) 1968 Series 2, vol. 1, pp. 878–879.

Donohue et al., "Correction of Single Photon or Particle Timing Measurements for Multiparticle Events", The Review of Scientific Instruments, vol. 43, No. 5, May 1972, pp. 791–796.

Birch et al., "Time–Domain Fluorescence Spectroscopy Using Time–Correlated Single–Photon Counting", Topics in Fluorescence Spectroscopy, vol. 1: Techniques, 1991, pp. 1–95.

*Primary Examiner*—F. L. Evans
*Attorney, Agent, or Firm*—Leydig, Voit & Mayer, Ltd.

[57] ABSTRACT

The present invention relates to a method and apparatus for efficiently measuring the lifetime of the fluorescence emitted from a fluorescent material in response to pulsed light. The measuring apparatus according to the present invention includes, at least, an excitation light source whose excitation power is regulated such that at least one fluorescence photon can be detected per light pulse on average. While repeatedly irradiating a sample containing the fluorescent material with excitation pulses of light from the excitation light source, a fluorescence detection time from irradiation to fluorescence detection and the number of detected fluorescence photons are measured for each excitation pulse of light. Then, on the basis of a data group composed of pairs of the measurement data of fluorescence photon detection time and fluorescence photon number, both of which are measured for each occurrence of excitation pulse of light, the lifetime and fluorescence decay curve of the fluorescence emitted from the fluorescent material are determined.

7 Claims, 3 Drawing Sheets

METHOD AND APPARATUS FOR MEASURING FLUORESCENCE

BACKGROUND OF THE INVENTION

1. Field of the Invention

The present invention relates to a method and apparatus for measuring fluorescence lifetime, which can efficiently determine the lifetime and fluorescence decay curve of the fluorescence generated from a fluorescent material irradiated with excitation light.

2. Related Background Art

Conventionally known as a method of measuring the lifetime of a fluorescent material contained in a sample is "time-correlated single-photon counting." The conventional time-correlated single-photon counting is introduced, for example, by David J. S. Birch and Robert E. Imhof, in: Topics in Fluorescence Spectroscopy, Vol. 1: Techniques (J. R. Lakowicz, ed.), pp. 1–95, Plenum Press, New York (1991). In time-correlated single-photon counting, the sample is irradiated with a pulse of light having such a weak excitation power that the average number of photons in the fluorescence detected per pulse of the excitation pulse of light is significantly smaller than 1 (e.g., 0.01), and then the fluorescence photon detection time, extending from when the sample is irradiated with the excitation pulse of light until the first fluorescence photon is detected is measured. While the irradiation with an excitation pulse of light is repeated, the fluorescence photon detection time is measured for each occurrence of an excitation pulse light, thereby producing a histogram concerning the fluorescence photon detection time. Then, the fluorescence lifetime is determined according to the obtained histogram. Here, a photomultiplier is usually used for detecting fluorescence photons.

SUMMARY OF THE INVENTION

Having studied the prior art mentioned above, the inventor has found the following problem. Namely, in the conventional time-correlated single photon counting, due to its principle, it is necessary that the number of fluorescence photons detectable per pulse of excitation pulse light be made very small (less than 1), so that the frequency of detection of fluorescence photons is not greater than a few percent of the number of excitation pulse light irradiation operations. As a result, a long period of measurement time is necessary to determine the fluorescence lifetime with a sufficient accuracy.

In order to overcome the above-mentioned problem, it is an object of the present invention to provide a method and apparatus for measuring fluorescence lifetime, which can efficiently measure the lifetime and fluorescence decay curve of the fluorescence excited by irradiation with excitation pulse light.

The measuring method and apparatus according to the present invention irradiates with pulse light a sample containing a fluorescent material which is an object to be measured, and measures the number of fluorescence photons excited with the pulse light and the like, thereby determining the lifetime of the fluorescence emitted from the fluorescent material.

In order to achieve the above-mentioned object, in the method according to the present invention, a sample containing a fluorescent material is repeatedly irradiated with excitation pulse light, the fluorescence photon detection time and the number of detected fluorescence photons are measured for each occurrence of irradiated excitation pulse light, and, on the basis of a measurement data group measured for each occurrence of irradiated excitation pulse light, the fluorescence lifetime is determined, with reference to a likelihood which uses as an unknown parameter at least a variable yielding the lifetime of the fluorescence emitted from the fluorescent material, from a value of the parameter which maximizes the likelihood.

Here, the fluorescence photon detection time is a period of time extending from when the sample is irradiated with the excitation pulse light until the first fluorescence photon from the fluorescent material exited with the excitation pulse light is detected. Each measurement data group includes a pair of the fluorescence photon detection time and data concerning the number of fluorescence photons both of which are measured for each occurrence of irradiated excitation pulse light.

In order to enable efficient measurement of the fluorescence lifetime, in the measuring method according to the present invention, the excitation power of the excitation pulse light reaching the sample is regulated to such an extent that at least one fluorescence photon can be detected per pulse on average.

The measuring apparatus realizing the above-mentioned measuring method comprises an excitation light source for repeatedly irradiating a sample with excitation pulse light, and a photodetector for detecting a fluorescence photon emitted from a fluorescent material. Here, the photodetector is preferably a multi-anode PMT (photomultiplier tube), which comprises a photocathode for receiving the fluorescence emitted from the fluorescent material and releasing photoelectrons by the number corresponding to the light quantity of the emitted fluorescence, an electron multiplying unit for multiplying the photoelectrons released from the photocathode and releasing secondary electrons, a plurality of anode electrodes each capturing the secondary electron arriving from the electron multiplying unit, and a vacuum envelope having an entrance window (including a faceplate) for transmitting therethrough the fluorescence from the fluorescent material and containing therein the photocathode, the electron multiplying unit, and the plurality of anode electrodes.

Further, the measuring apparatus according to the present invention comprises a time measuring system for measuring the fluorescence photon detection time for each excitation pulse irradiated from the excitation light source; a fluorescence photon number measuring system for measuring, for each excitation pulse irradiated from the excitation light source, of the plurality of anode electrodes, the number of anode electrodes which have outputted an electric signal in response to the captured secondary electron as the number of fluorescence photons to be detected; and a fluorescence lifetime determining system for determining, on the basis of the measurement data group measured for each occurrence of irradiated pulse light, at least the lifetime of the fluorescence emitted from the fluorescent material. Specifically, the fluorescence lifetime determining system determines the fluorescence lifetime, with reference to a likelihood which uses as an unknown parameter at least a variable yielding the lifetime of the fluorescence emitted from the fluorescent material, from a value of the parameter which maximizes the likelihood.

Here, in order to enable efficient measurement of the fluorescence lifetime, the excitation light source regulates the excitation power of the excitation pulse light reaching the sample to such an extent that at least one fluorescence photon can be detected per pulse on average. On the other hand, in order for the number of anode electrodes each outputting an electric signal in response to the secondary electron that has arrived and the number of fluorescence photons emitted from the fluorescent material irradiated with the excitation pulse light to substantially correspond to each other, the number of fluorescence photons incident on the photodetector must be smaller than the number of anode electrodes prepared. Hence, the excitation light source regulates the excitation power of the excitation pulse light reaching the sample to such an extent that the number of fluorescence photons to be detected per pulse would not exceed the number of anode electrodes.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

In the following, the method and apparatus for measuring fluorescence lifetime according to the present invention will be explained in detail with reference to FIGS. 1 to 3. In the explanation of drawings, constituents identical to each other will be referred to with numerals identical to each other, without repeating overlapping descriptions.

Figure 1:
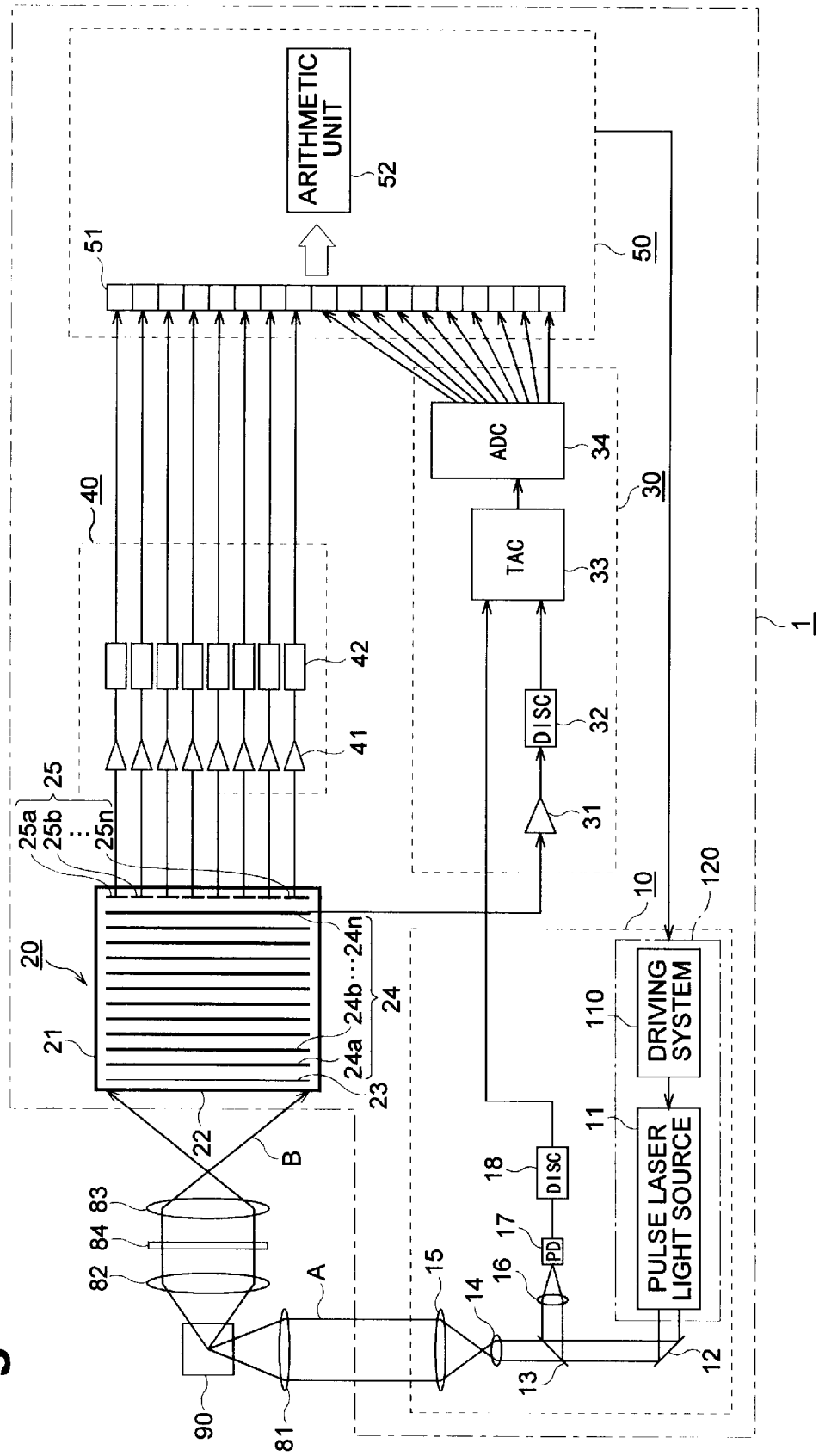
FIG. 1 is a view showing a configuration of an embodiment of the apparatus for measuring fluorescence lifetime according to the present invention.

FIG. 1 is a view showing a configuration of the apparatus for measuring fluorescence lifetime according to this embodiment. This measuring apparatus 1 comprises an excitation light source system 10 for outputting excitation pulse light A so as to reach a sample 90 containing a fluorescent material; a photodetector 20 for detecting fluorescence B generated from the sample 90 and outputting a current pulse signal; a time measuring system 30 for measuring, for each occurrence of the irradiated pulse light, the fluorescence photon detection time extending from when the excitation pulse light A irradiates the sample 90 until the first fluorescence photon is detected by the photodetector 20; a fluorescence photon number measuring system 40 for measuring, for each pulse irradiated, the number of fluorescence photons detected by the photodetector 20 on the basis of the current pulse signal outputted from the photodetector 20; and a fluorescence lifetime determining system 50 for determining the fluorescence lifetime and fluorescence decay curve on the basis of the fluorescence photon detection time measured by the time determining system 30 and the number of fluorescence photons detected by the fluorescence photon number measuring system 40.

The excitation light source system 10 comprises an excitation light source 120 including a pulse laser light source 11 and a driving system 110, a photodiode 17, a pulse-height discriminator 18, and the like. The pulse laser light source 11 repeatedly outputs excitation pulse light. A reflector 12 reflects the excitation pulse light. A beam splitter 13 reflects a part of the excitation pulse light reflected by the reflector 12 while transmitting the remainder therethrough. Lenses 14 and 15 collimate and output the excitation pulse light transmitted through the beam splitter 13. On the other hand, a lens 16 collects the excitation pulse light reflected by the beam splitter 13, whereas the photodiode 17 receives thus collected excitation pulse light and outputs a current signal in response to the light quantity thereof. The pulse-height discriminator 18 feeds the electric signal therein and outputs a timing signal indicative of the time at which the excitation pulse light is outputted.

The excitation pulse light A transmitted through the beam splitter 13 of the excitation light source system 10 is collected by a lens 81 so as to irradiate the sample 90. The fluorescence B consequently generated from the fluorescent material contained in the sample 90 is collected by a lens 82 and, after passing through a band-pass filter 84 to eliminate its undesirable scattered light component and the like, is substantially uniformly made incident on nearly the whole face of the entrance window 22 of the photodetector 20 by way of a lens 83.

The photodetector 20 comprises a vacuum envelope 21 having the entrance window 22 for transmitting the fluorescence B therethrough. Disposed within the vacuum envelope 21 is a photocathode 23 for releasing photoelectrons by a number corresponding to the Light quantity of the incident fluorescence B, an electron multiplying unit 24 constituted by a plurality of stages (11 stages in this drawing) of dynodes 24a to 24n for successively multiplying the photoelectrons and generating a number of secondary electrons, and an anode 25 composed of a plurality of (8 in this embodiment) anode electrodes 25a to 25n. Each of the anode electrodes 25a to 25n is arranged like an array within a plane in parallel to the photocathode 23. The electron multiplying unit 24 may be either a multistage mesh dynode unit applicable to a photomultiplier or a microchannel plate, for example.

In the photodetector 20, the photocathode 23 is set to a lower potential as compared with the anode electrodes 25a to 25n. When the fluorescence B is incident on the photocathode 23 while a predetermined voltage is applied to each of the dynodes 24a to 24n, photoelectrons are released from the photocathode 23 by a number corresponding to the light quantity of the incident fluorescence B. These photoelectrons are successively multiplied by the individual dynodes 24a to 24n, thereby a number of secondary electrons are generated. Each of the secondary electrons reaches one of the prepared anode electrodes 25a to 25n (8 pieces in this embodiment). At this time, the secondary electrons are multiplied in the individual dynodes 24a to 24n while keeping their positional relationship upon the fluorescence photon incidence, i.e., photoelectron release, on the photocathode 23. Consequently, the anode electrode outputting a current pulse signal in response to a secondary electron arriving there corresponds to the position where a photon of the fluorescence B is incident on the photocathode 23.

The time measuring system 30 comprises an amplifier 31, a pulse-height discriminator 32, a time-to-amplitude converter 33, and an AD converter 34. The amplifier 31 feeds therein the pulse signal outputted from the dynode 24n arranged at the last stage of the photodetector 20, converts this pulse signal into a voltage pulse signal, amplifies this voltage pulse signal, and outputs thus amplified signal. Here, the amplifier 31 feeds therein the pulse signal outputted from the last-stage dynode 24n since this dynode is common to a plurality of anode electrodes 25a to 25n. The pulse-height discriminator 32 feeds therein the voltage pulse signal outputted from the amplifier 31, and outputs a timing signal when this voltage pulse signal becomes over a predetermined threshold voltage. Namely, the timing signal outputted from this pulse-height discriminator 32 indicates the timing at which a photon of the fluorescence B is detected by the photodetector 20. The time-to-amplitude converter 33 feeds therein the respective timing signals outputted from the pulse-height discriminators 18 and 32, and outputs, on the basis of these two timing signals, a voltage signal having a value corresponding to the fluorescence photon detection time extending from when the sample 90 is irradiated with the excitation pulse light A until the first photon of the fluorescence B is detected by the photodetector 20. The AD converter 34 feeds therein the voltage signal outputted from the time-to-amplitude converter 33, converts it into a digital signal corresponding thereto, and outputs this digital signal. The digital signal outputted from the AD converter 34 indicates the fluorescence photon detection time.

The fluorescence photon number measuring system 40 comprises the same number of sets of amplifiers 41 and pulse-height discriminators 42 as the number of the anode electrodes 25a to 25n in the photodetector 20. In this drawing, 8 sets of amplifiers 41 and pulse-height discriminators 42 are provided, such that the respective sets correspond to the prepared anode electrodes 25a to 25n. Each amplifier 41 feeds therein the current signal outputted from its corresponding one of the anode electrode, 25a to 25n, converts it into a voltage pulse signal, amplifies the voltage pulse signal, and outputs thus amplified signal. The pulse-height discriminators 42 feed therein the voltage pulse signals outputted from the amplifiers 41, discriminate those having a peak level higher than a predetermined threshold voltage, and output logical pulse signals. Namely, the pulse-height discriminators 42 output a logical pulse signal only when a current pulse signal having a peak level corresponding to at least one fluorescence photon of the fluorescence B to be measured is outputted from any of the anode electrodes 25a to 25n. As a consequence, of the 8 pieces of pulse-height discriminators 42, the number of those that have outputted logical pulse signals corresponds to the number of photons of the fluorescence B detected by the photodetector 20.

The fluorescence lifetime determining system 50 feeds therein, via an interface 51, the digital signal outputted from the AD converter 34 of the time measuring system 30 and the respective logical pulse signals outputted from the individual pulse-height discriminators 42 of the fluorescence photon number measuring system 40, and determines, at an arithmetic unit 52, the fluorescence lifetime and fluorescence decay curve of the fluorescence B according to the digital signal and logical pulse signals.

In the following, the contents of processing in the arithmetic unit 52 in the fluorescence lifetime measuring system 50 will be explained together with the operation of the fluorescence lifetime measuring apparatus 1 of FIG. 1. Also, an embodiment of the method of measuring fluorescence lifetime according to the present invention will be explained.

The excitation pulse light A repeatedly outputted from the pulse laser light source 11 in the excitation light source system 10 irradiates the sample 90 by way of the reflector 12, beam splitter 13, and lenses 14, 15, and 81. The fluorescence B generated from the fluorescent material in the sample 90 upon irradiation with the excitation pulse light A is substantially uniformly made incident on nearly the whole face of the entrance window 22 of the photodetector 20 by way of the lens 82, band-pass filter 84, and lens 83. In the photodetector 20, when the fluorescence B is made incident on the photocathode 23 through the entrance window 22, a photon is released from the photocathode 23, its secondary electron is multiplied by the electron multiplying unit 24 comprising a plurality of stages of dynodes 24a to 24n, thus multiplied secondary electron is made incident on one of a plurality of anode electrodes 25a to 25n, and a current pulse signal is outputted from the anode electrode (active anode electrode) on which the secondary electron has been made incident. The current pulse signal outputted from the active anode electrode is converted into a voltage pulse signal by the amplifier 41 corresponding to the active anode electrode in tile fluorescence photon number measuring system 40. This voltage pulse signal is fed into the corresponding pulse-height discriminator 42, thereby a logical pulse signal is outputted. Here, when the number of active anode electrodes outputting logical pulse signals per pulse of the excitation pulse light A is sufficiently smaller than the number of anode electrodes 25a to 25n provided in the photodetector 20, the number of active anode electrodes which have outputted logical pulse signals may be assumed to be identical to the number of fluorescence photons detected by the photodetector 20.

On the other hand, a part of the excitation pulse light outputted from the pulse laser light source 11 is reflected by the beam splitter 13 and is received by the photodiode 17 through the lens 16, thereby the pulse-height discriminator 18 outputs a timing signal indicative of the timing at which the excitation pulse light A has been outputted. Also, on the basis of the pulse signal outputted from the dynode arranged at the last stage of the electron multiplying unit 24 in the photodetector 20, the amplifier 31 and pulse-height discriminator 32 generate a timing signal indicative of the timing at which a photon of the fluorescence B has been detected by the photodetector 20. In accordance with the respective timing signals outputted from the pulse-height discriminators 18 and 32, the time-to-amplitude converter 33 outputs a voltage signal having a value corresponding to the fluorescence photon detection time extending from when the sample 90 was irradiated with the excitation pulse light A until the first photon of the fluorescence B was detected by the photodetector 20, and the AD converter 34 outputs a digital signal corresponding to the voltage signal outputted from the time-to-amplitude converter 33.

For each occurrence of the excitation pulse light A repeatedly outputted from the pulse laser light source 11, the respective logical pulse signals outputted from the individual pulse-height discriminators 42 in the fluorescence photon number measuring system 40 and the digital signal outputted from the AD converter 34 in the time measuring system 30 are transmitted to the arithmetic unit 52 via the interface 51 of the fluorescence lifetime determining system 50. In the arithmetic unit 52, the number of fluorescence photons detected by the photodetector 20 is determined on the basis of the logical pulse signals inputted from the fluorescence photon number measuring system 40, and the fluorescence photon detection time extending from when the sample 90 was irradiated with the excitation pulse light A until the first fluorescence photon was detected by the photodetector 20 is determined on the basis of the digital signal inputted from the time measuring system 30. Into the arithmetic unit 52, for each of numerous (hereinafter assumed to be N) pulses of the excitation pulse light A, the fluorescence photon number $n_i$ and the fluorescence photon detection time $T_i$ (i=1, 2, 3, . . . , N) are stored as a pair.

In the arithmetic unit 52, by use of the measurement data group, i.e., measurement data comprising N pieces each of fluorescence photon number $n_i$ and fluorescence photon detection time $T_i$ (i=1, 2, 3, . . . , N), the fluorescence lifetime and fluorescence decay curve of the fluorescence B are determined. In general, a model of fluorescence decay curve is given by a single exponential function or the sum of a plurality of exponential functions. Also, while a fluorescence decay curve is represented by a relationship between measurement time and measured fluorescence intensity (fluorescence photon number per unit time), the fluorescence intensity is equivalent to the counting rate in actual measurement and to the counted value after counting for a predetermined time.

Further, the measuring environment may include the case where the sample to be measured contains a plurality of fluorescent materials while the fluorescence decay curve of the fluorescent materials is expressed by the sum of two exponential functions, the case where the sample to be measured contains two kinds of fluorescent materials each expressed by a single exponential function, the case where the sample to be measured contains two kinds of fluorescent materials respectively expressed by a single exponential function and the sum of a plurality of exponential functions, or the like.

Consequently, when the following sum of two exponential functions:

$$P(t) = \frac{\lambda_1 \lambda_2}{A\lambda_1 + \lambda_2} \{\exp(-\lambda_1 t) + A\exp(-\lambda_2 t)\}$$

is employed as a model of fluorescence decay curve, the parameters characterizing this model are $\lambda_1$, $\lambda_2$, and A. Since fluorescence lifetimes are given by $1/\lambda_1$ and $1/\lambda_2$, on the other hand, determining the fluorescence lifetimes in such a manner also means determining the fluorescence decay curve.

Explained in the following is the case where the fluorescence decay curve of the fluorescence B generated from the fluorescent material in the sample 90 is represented by the sum of two exponential functions having fluorescence lifetimes different from each other.

Let the two fluorescence lifetimes be $1/\lambda_1$ and $1/\lambda_2$ ($\lambda_2 = A\lambda_1$), respectively. Also, with reference to the time at which the sample 90 is irradiated with each pulse of the excitation pulse light A (time t=0), the probability of photons of the fluorescence B being detected by the photodetector 20 during the period from time t to time t +dt is assumed to be given by the following expression (1)

$$p(t)dt = \frac{1}{2}\{\lambda_1 \exp(-\lambda_1 t) + \lambda_2 \exp(-\lambda_2 t)\}dt \quad (1)$$

In the arithmetic unit 52, according to the N pairs of fluorescence photon number $n_i$ and fluorescence photon detection time $T_i$ (i=1, 2, 3, . . . , N), the logarithmic likelihood represented by the following expression (2):

$$\log L = \sum_{i=1}^{N} \log\{P(T_i \mid n_i)\} \quad (2)$$

is calculated. Here, P(T|n) is the probability density of the first fluorescence photon being detected during the period from time T to time T+dT in the case where n pieces of fluorescence photons are detected, which is given by the following expression (3):

$$P(T|n)dT = np(T)dT\{\int_T^\infty p(t)dt\}^{n-1} \quad (3)$$

Consequently, the logarithmic likelihood of the above-mentioned expression (2) is represented by the following expression (4):

$$\log L = \sum_{i=1}^{N} \left\{ \log n_i + \log\{p(T_i)\} + (n_i - 1)\log\left(\int_{T_i}^\infty p(t)dt\right) \right\} \quad (4)$$

Then, the arithmetic unit 52 obtains the respective values of $\lambda_1$ and $\lambda_2$ maximizing the logarithmic likelihood represented by the above-mentioned expression (4), and then determines the respective values of fluorescence lifetimes $1/\lambda_1$ and $1/\lambda_2$ or the fluorescence decay curve. Here, in the determination by maximizing the logarithmic likelihood, a typical optimization algorithm such as quasi-Newton's method is preferably used.

The results of a simulation concerning fluorescence lifetime estimation will now be explained. In the following, the value of $\lambda_1$, the value of $\lambda_2$, and the average number of fluorescence photons detected per pulse of excitation pulse light are assumed to be 2.0, 1.0, and 2.0, respectively. Also, the value of N is assumed to be one hundred thousand.

Figure 2:
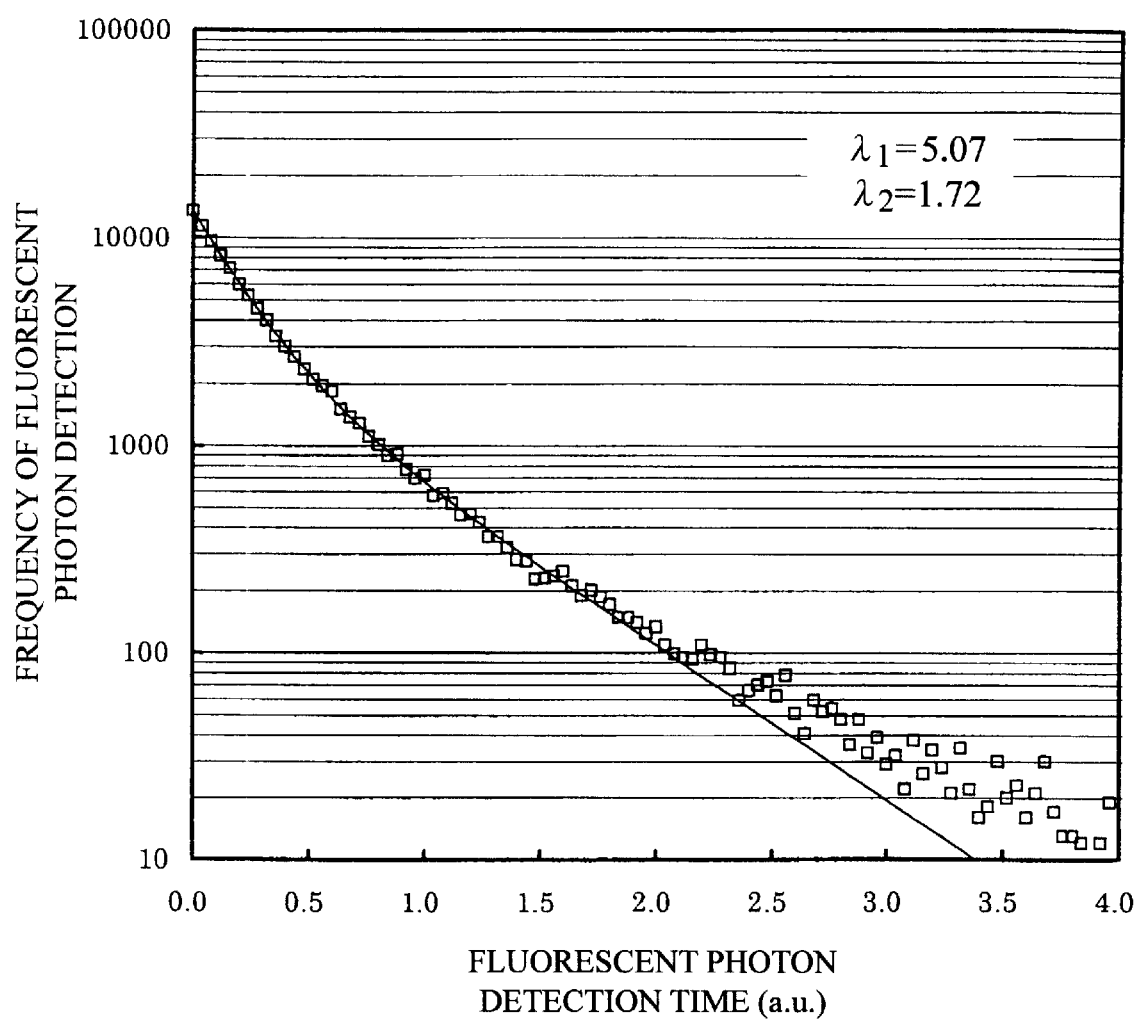
FIG. 2 is a graph showing results of a simulation of a fluorescence lifetime determination by conventional time-correlated single-photon counting.

FIG. 2 is a graph showing the results of a simulation of fluorescence lifetime estimation by the conventional time-correlated single-photon counting. This graph represents, as a histogram, the frequency of the fluorescence photon detection time extending from when the sample is irradiated with each pulse of excitation pulse light until the first fluorescence photon is detected. Each square symbol in the graph indicates a value of the simulation results, whereas the curve in the graph indicates the results of least-square fitting concerning the above-mentioned expression (1). According to this graph, 5.07 and 1.72 are obtained as the values of $\lambda_1$ and $\lambda_2$, respectively, both of which greatly differ from their values originally set.

Figure 3:
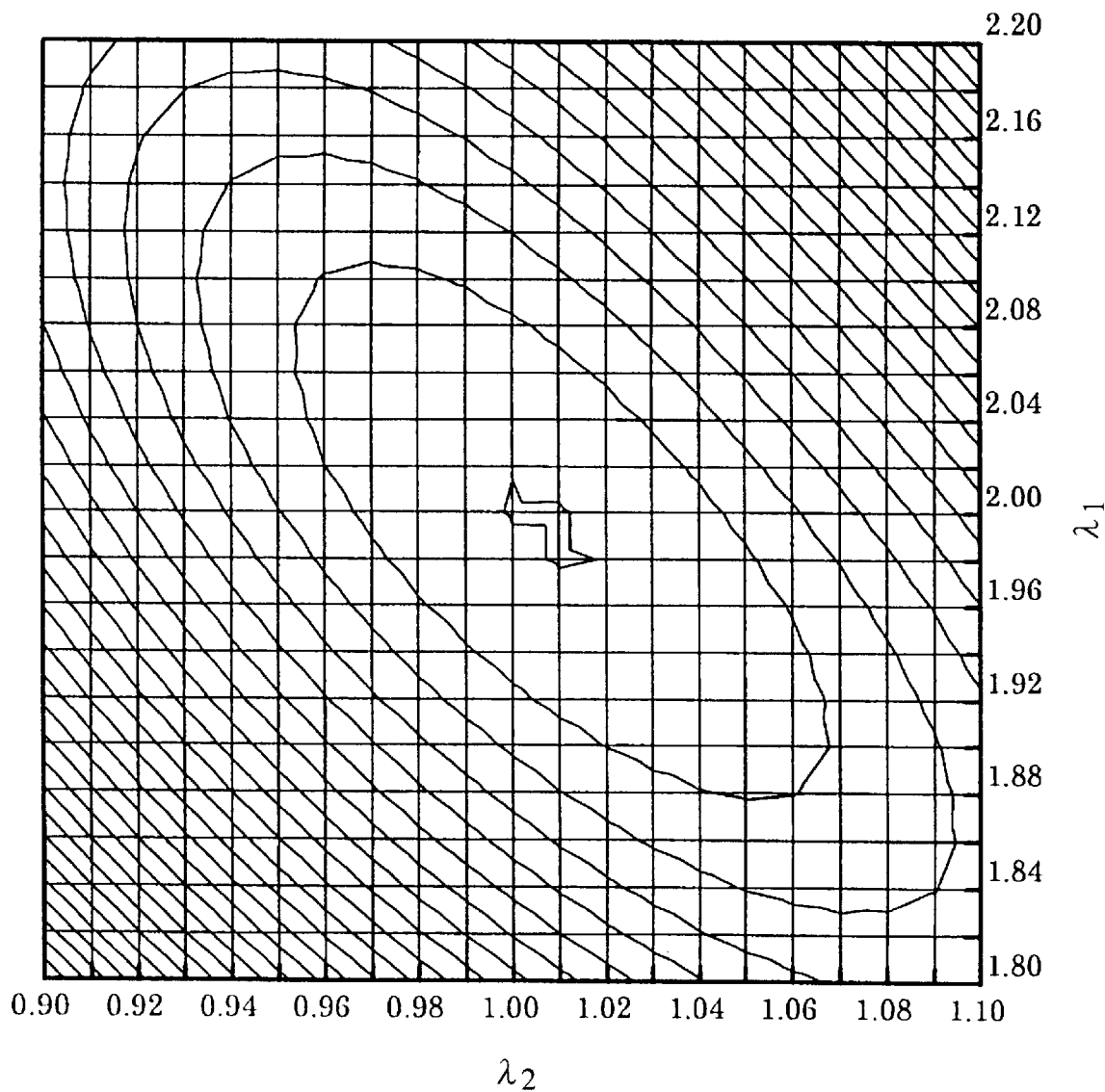
FIG. 3 is a graph showing results of a simulation of a fluorescence lifetime determination by an embodiment of the method of measuring fluorescence lifetime according to the present invention.

On the other hand, FIG. 3 is a graph showing results of a simulation of fluorescence lifetime estimation by the method of measuring fluorescence lifetime according to this embodiment. In this graph, the parameters $\lambda_1$ and $\lambda_2$ of the logarithmic likelihood represented by the above-mentioned expression (4) are shown in the form of contour lines. As can be seen from this graph, the logarithmic likelihood (expression (4)) is maximized in the vicinity of $(\lambda_1, \lambda_2) = (2.0, 1.0)$, thus indicating an excellent accuracy in estimation.

Without being restricted to the above-mentioned embodiment, the present invention can be modified in various manners. For example, though 8 sets each of the plurality of anode electrodes 25a to 25n, amplifiers 41, and pulse-height discriminators 42 are provided in the fluorescence lifetime measuring apparatus according to the above-mentioned embodiment, without being restricted thereto, the number of sets may also be 16, 64, or the like. As explained in detail in the foregoing, in accordance with the present invention, a sample is repeatedly irradiated with excitation pulse light and, for each occurrence of the excitation pulse light irradiation, while measuring the fluorescence photon detection time extending from when the sample is irradiated with the excitation pulse light until the first fluorescence photon is detected, the number of detected fluorescence photons is measured. Then, on the basis of the fluorescence photon detection time and number of fluorescence photons measured for each occurrence of excitation pulse light irradiation, the fluorescence lifetime and fluorescence decay curve are determined. As a consequence, even when the number of fluorescence photons detected per pulse of excitation pulse light is not smaller than 1 on average, the fluorescence lifetime and fluorescence decay curve can accurately be determined. Also, the present invention can yield a fluorescence photon detection frequency which is higher than that in accordance with the conventional time-correlated single photon counting by at least one order of magnitude, thus being capable of efficiently measuring the fluorescence lifetime and fluorescence decay curve in a short period of time.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A method of determining lifetime of fluorescence emitted from a fluorescent material contained in a sample by use of pulsed excitation light, said method comprising:

repeatedly irradiating a sample with pulses of excitation light;

measuring, for each occurrence of irradiation by a pulse of excitation light, a fluorescence detection time extending from when the sample is irradiated with a pulse of excitation light until a fluorescence photon from the fluorescent material excited by the excitation pulse of light is detected, and the number of fluorescence photons detected; and determining at least the lifetime of the fluorescence emitted from the fluorescent material from a measurement data group measured for each occurrence of irradiation by an excitation pulse of light, the measurement data group including data concerning the fluorescence photon detection time and data concerning the number of fluorescence photons, both measured for each occurrence of irradiation by an excitation pulse of light.

2. The method according to claim 1, wherein the lifetime of the fluorescence emitted from the fluorescent material is determined, with reference to a likelihood which includes the measurement data and a variable yielding the lifetime of the fluorescence as an unknown parameter, from a value of the unknown parameter which maximizes the likelihood.

3. The method according to claim 1, wherein the excitation power of the excitation pulse of light reaching the sample is regulated so that at least one fluorescence photon can be detected per excitation light pulses, on average.

4. An apparatus for determining lifetime of fluorescence emitted from a fluorescent material contained in a sample by use of pulses of excitation light, said apparatus comprising:

an excitation light source for repeatedly irradiating a sample with pulses of excitation light;

a photodetector for detecting a fluorescence photon emitted from the fluorescent material, said photodetector comprising a photocathode for receiving the fluorescence emitted from the fluorescent material and releasing photoelectrons in a number corresponding to intensity of the emitted fluorescence, an electron multiplying unit for multiplying the photoelectrons released from said photocathode and releasing secondary electrons, a plurality of anode electrodes, each anode electrode capturing the secondary electrons arriving from said electron multiplying unit, and a vacuum envelope having an entrance window transmitting the fluorescence from the fluorescent material and containing said photocathode, said electron multiplying unit, and said plurality of anode electrodes;

a time measuring system for measuring, for each excitation pulse radiated by said excitation light source, a fluorescence photon detecting time extending from when the sample is irradiated with the excitation pulse of light until a fluorescence photon from the fluorescent material excited by the excitation pulse of light is detected;

a fluorescence photon number measuring system for measuring, for each excitation pulse of light radiated by said excitation light source, of said plurality of anode electrodes, the number of anode electrodes which have output an electric signal in response to a captured secondary electron as the number of fluorescence photons detected; and a fluorescence lifetime determining system for determining at least the lifetime of the fluorescence emitted from the fluorescent material from a measurement data group measured for each occurrence of an irradiated pulse of light, said measurement data group including data concerning the fluorescence photon detection time and data concerning the number of fluorescence photons, both measured for each occurrence of a radiated excitation pulse of light.

5. The apparatus according to claim 4, wherein said fluorescence lifetime determining system determines at least the lifetime of the fluorescence emitted from the fluorescent material with reference to a likelihood which includes the measurement data and a variable yielding the lifetime of the fluorescence as an unknown parameter, from a value of the unknown parameter which maximizes the likelihood.

6. The apparatus according to claim 4, wherein said excitation light source regulates excitation power of the excitation pulses of light reaching the sample so that at least one fluorescence photon can be detected per excitation pulse of light, on average.

7. The apparatus according to claim 4, wherein said excitation light source regulates excitation power of the excitation pulses of light reaching the sample so that the fluorescence photons detected per excitation pulse of light does not exceed the number of said anode electrodes.

* * * * *